United States Patent [19]

Ueda et al.

[11] 4,154,956
[45] May 15, 1979

[54] METHOD FOR PRODUCING LYSINE ESTER

[75] Inventors: Toshiaki Ueda; Shinzo Imamura, both of Nagoya, Japan

[73] Assignee: Toray Industries, Inc., Tokyo, Japan

[21] Appl. No.: 807,218

[22] Filed: Jun. 16, 1977

Related U.S. Application Data

[63] Continuation of Ser. No. 532,526, Dec. 13, 1974, abandoned.

[30] Foreign Application Priority Data

Dec. 21, 1973 [JP] Japan .................................. 48-142357
Dec. 21, 1973 [JP] Japan .................................. 48-142359

[51] Int. Cl.$^2$ ............................................ C07C 101/26
[52] U.S. Cl. ................................................... 560/169
[58] Field of Search ......................................... 560/169

[56] References Cited

U.S. PATENT DOCUMENTS 2,543,345  2/1951  Waller ................................... 560/169
3,211,781  10/1965  Taub ..................................... 560/169

FOREIGN PATENT DOCUMENTS 75-93921  7/1975  Japan.

OTHER PUBLICATIONS

Marvel, J. Am. Chem. Soc., 68, pp. 1681–1686, (1946).

Primary Examiner—Bernard Helfin
Assistant Examiner—Michael Shippen
Attorney, Agent, or Firm—Miller & Prestia

[57] ABSTRACT

Lysine ester is produced by heating $\alpha$-amino-$\epsilon$-caprolactam with an alcohol. The reaction can be accelerated by adding a small amount of water and an acid or base catalyst.

9 Claims, No Drawings

METHOD FOR PRODUCING LYSINE ESTER

This is a continuation, of application Ser. No. 532,526, filed Dec. 13, 1974, now abandoned.

BACKGROUND OF THE INVENTION a. Field of the Invention.

The present invention relates to a method for producing lysine ester from α-amino-ε-caprolactam.

b. Description of the Prior Art.

Lysine ester has been used as a synthetic intermediate for producing a monomer of polyurethane having no yellow coloring, which is an additive for polyamides and various medicines.

Lysine ester has been produced by esterification of lysine in the presence an acid catalyst. This method, however, is not necessarily satisfactory for commercial production of lysine ester, because the starting material, lysine, is very expensive. Furthermore, in the esterification of lysine, the reaction rate is gradually reduced corresponding to dilution of alcohol, which is used as both reactant and solvent, by the production of water from esterification reaction, and therefore it is difficult to complete the reaction. The recovery of alcohol from waste containing also water and an acid catalyst such as hydrochloric acid is another problem in this method.

An object of the present invention is to provide a novel method to produce lysine ester. Another object of the present invention is to produce lysine ester directly from α-amino-ε-caprolactam in a high yield and conversion.

SUMMARY OF THE INVENTION

We have found that lysine ester can be produced by heating α-amino-ε-caprolactam with an alcohol optionally in the presence of acid or base catalysts. We also have found that this reaction can be accelerated by adding a small amount of water.

DESCRIPTION OF PREFERRED EMBODIMENTS

The starting material for the method of this invention, α-amino-ε-caprolactam is a well known compound, and is used as an intermediate for production of synthetic lysine.

This compound can be prepared from ε-caprolactam.(British Pat. Nos. 901,169 867,269, and 856,967)

An alcohol, another starting material for the method of this invention, may be selected from the group consisting of primary and secondary lower non-aromatic alcohols represented by a general formula R–OH wherein R is an alkyl or cycloalkyl group having 1 to 10 carbon atoms.

The examples of alcohol, which may be used in the present invention, are as follows; methanol, ethanol, propanols, n-octanol, cyclopentyl alcohol, cyclohexyl alcohol etc. The preferable examples are methanol, ethanol and propanols.

The alcohol used in the present invention may usually be decided from the view point of what kind of lysine ester is desired. For example when the lysine ester is used as a raw material for non-yellow-coloring polyurethane, a suitable alcohol is methanol or ethanol.

In the present invention the reaction is carried out in the liquid phase and under atmospheric or elevated pressure. A solvent may be used if it is chemically inert to α-amino-ε-caprolactam, alcohol and a catalyst which may be optionally used. From the practical point of view, however, a solvent having a boiling point of 60° C. to 250° C. may be preferably used.

A large excess of the reactant alcohol may act as the role of solvent. The examples of preferable solvents are as follows; ethers such as tetrahydrofuran and diglyme, chlorinated hydrocarbons such as chloroform, carbon tetrachloride and ethylene chloride and aromatic hydrocarbons such as benzene, toluene and xylene.

The reaction temperature is 40° to 250° C. and preferably 50° to 200° C. In order to accelerate the reaction, high reaction temperature is preferable, but at a temperature of higher than 250° C., α-amino-ε-caprolactam and lysine ester are ready to suffer thermal decomposition.

The reaction is usually carried out under a pressure of from atmospheric to 30 Kg/cm$^2$, and the reaction period is usually 0.5 to 80 hours.

The amount of alcohol used may be preferably 5 to 200 mole per mole of α-amino-ε-caprolactam. One mole of alcohol is stoichiometrically equivalent to one mole of α-amino-ε-caprolactam, and may theoretically complete the reaction of this invention. However, use of an excess amount of alcohol is preferably for the purpose of acceleration of the reaction and in order to bring the equilibrium point to product side. From the practical point of view, the amount of alcohol may be more preferably 5 to 50 mole per mole of α-amino-ε-caprolactam.

During the reaction, α-amino-ε-caprolactam forms a solid salt with the acid catalyst so that when an amount of alcohol is less than 5 moles, the reaction mixture is too concentrated and a viscous slurry is obtained which has poor processability whereby a good yield cannot be obtained.

The reaction of this invention may take place without catalyst, but use of it is preferable. Either an acid catalyst or base catalyst is effective for the reaction. The examples of acid catalysts are mineral acids such as hydrochloric acid, sulfuric acid and phosphoric acid; solid acid catalysts such as zeolites and cation exchange resins, organic acids such as p-toluenesulfonic acid, benzenesulfonic acid and trifluoroacetic acid; Lewis acids such as boron trifluoride, etc. Among these acid catalysts hydrochloric acid and cation exchange resins are most preferable because they readily form a salt with both the starting material and product of this invention. The acid catalysts may be consumed to form a salt with α-amino-ε-caprolactam and lysine ester. The amount of acid, which acts as an acid catalysts, may be preferably more than 0.01 mole per mole of α-amino-ε-caprolactam.

The examples of base catalyst are alcoholates such as sodium methylate, sodium ethylate, potassium methylate and potassium ethylate, and amines such as 1,5-diazo-bicyclo (4,3,0) nonene-5, triethylamine, 1,8-diazobicyclo (5,4,0) undecene-7 and dicyclohexyl ethyl amine etc. The amount of these base catalysts may be preferably more than 0.01 mole per mole of α-amino-ε-caprolactam. An acid catalyst is preferably used when α-amino-ε-caprolactam is fed to the reaction mixture in a form of a salt with an acid. The same acid as added in a form of the salt is preferably used as a catalyst.

Addition of water to the reaction mixture is also effective to accelerate the reaction of the present invention.

The amount of water present may be up to 2 moles; preferably 0.01 to 2 moles and, more preferably 0.05 to 1 mole per mole of the alcohol is used. The water may be either separately added to the reaction mixture, or fed with alcohol as a solution. When too much water is added to the reaction mixture, α-amino-ε-caprolactam is hydrolized to lysine and the yield of lysine ester is reduced. Too much water also makes it difficult to crystallize out the lysine ester salt from the reaction mixture in the separation step which follows because of the high solubility of the lysine ester salt in water.

The reaction of this invention may be carried out either batchwise or continuously. After the reaction is over, lysine ester is separated from the reaction mixture according to a conventional method; for example, passing the reaction mixture through an ion exchange resin column or cooling the mixture followed by a liquid-solid separation procedure.

The lysine ester may be preferably crystallized out of solution in a form of salt with an acid; most preferably with hydrochloric acid. When the reaction is carried out in the absence of catalyst or in the presence of base catalyst, the reaction mixture may be preferably neutralized by addition of hydrochloric acid, and thereafter the lysine ester is separated from the reaction mixture in a form of a hydrochloric acid salt.

Especially when lysine methyl or ethyl ester is desired, the hydrochloric acid salt of those lysine esters is easily crystallized out from the reaction mixture by cooling. In that case the method of this invention may be most preferably carried out in the presence of water and a catalytic amount of hydrochloric acid. After the crystallized lysine ester is separated from the reaction mixture by a conventional method, the mother liquor still containing any lysine ester or its hydrochloric acid salt, and any small amount of unreacted starting material present may be recycled to the reaction zone. The crude lysine ester salt thus obtained may be easily purified by washing with cold alcohol. Thus, according to the present invention, lysine ester can be easily produced in a high yield.

The present invention can be further illustrated by the following examples of preferred embodiments.

EXAMPLE 1

2.00 grs. of α-amino-ε-caprolactam hydrochloride (12.0 mili moles), 38.2 grs. of methanol (1.2 moles), and 6.55 grs. of HCl (0.17 mole) were charged into the 100 milliliter glass ampule, and heated for 10 hrs. in the 120° C. oil bath. The ampule was then cooled to the room temperature, and the contents were taken out from the ampule.

The solution obtained was cooled in an ice-bath, and then 1.5 grs. of crystalline material was obtained by filtration. The lysine methyl ester dihydrochloride was found to be contained as 92 mole % in the crystalline material by NMR spectrum measured in $D_2O$ solvent.

The crystalline material in methanol, and neutralized to about pH 8.0 by sodium methylate-methanol solution. The solution, thus obtained, was passed through the 20mmφ × 50cm weak cation exchange column, Amberlite IRC-50, freed from water before use. Almost all unreacted α-amino-ε-caprolactam hydrochloride and a small amount of unneutralized lysine methyl ester dihydrochloride were eluted.

Then 1.3 grs. of lysine methyl ester dihydrochloride was obtained by charging methanolic hydrochloride into the weak cation exchange column. (yield 46.5%)

EXAMPLE 2

The same reaction as Example 1 was carried out, using ethanol instead of methanol. The reaction was continued for 20 hrs.

The contents, taken out from the glass ampule, were neutralized to about pH 8.0 by adding sodium ethylate-ethanol solution, and the mixture of α-amino-ε-caprolactam hydrochloride, lysine ethyl ester monohydrochloride, and a small amount of lysine ethyl ester dihydrochloride, was obtained. α-amino-ε-caprolactam hydrochloride, lysine ethyl ester dihydrochloride, and sodium chloride were eluted by passing the mixture through the weak cation exchange column, Amberlite IRC-50, freed from water before use, and washing the column with ethanol. Then, 1.18 grs. of lysine ethyl ester monohydrochloride was eluted in the form of the dihydrochloride salt by charging ethanolic hydrochloride into the weak cation exchange column. (yield 40%)

EXAMPLE 3

16.46 grs of α-amino-ε-caprolactam hydrochloride (0.1 mole), and 160 grs. of methanol (5.0 moles) were charged into the 0.5 liter autoclave (made of SUS 304) and heated at 120° C. for 20 hrs. with stirring.

After cooling to the room temperature, the contents were passed through the cation exchange column (IRC-50, freed from water before use).

13.17 grs. of unreacted α-amino-ε-caprolactam hydrochloride (0.08 mole) was contained in the eluted solution.

4.66 grs. of lysine methyl ester dihydrochloride (0.02 mole) was obtained by passing methanolic hydrochloride through the cation exchange column. (yield 20%)

EXAMPLE 4

12.82 grs. of α-amino-ε-caprolactam (0.1 mole), 64 grs. of methanol, and 5.4 grs. of sodium methylate (0.1 mole) were charged into the 0.5 liter autoclave (made of SUS 304), and heated for 7 hrs. at 120° C.

The autoclave was cooled to the room temperature, and the contents were taken out from the reactor. 7.3 grs. of HCl (0.2 mole) in methanol were added to the reaction mixture, and passed through the same weak cation exchange column as Example 1.

After the elution of sodium chloride, and unreacted α-amino-ε-caprolactam, methanolic hydrochloride was charged into the column, and then 6,99 grs. of lysine methyl ester dihydrochloride (0.03 mole) was obtained. (yield 30%)

EXAMPLE 5

To the solution containing 16.46 grs, of α-amino-ε-caprolactam hydrochloride (0.1 mole), 164 grs. of methanol (5 moles), and 23.07 grs. of HCl (0.1 mole), various amounts, as shown in the following Table 1, of water was separately added. The solution, thus prepared, was charged into a 0.5 liter four necked flask equipped with a cooler, and heated at 67° C. for 20 hrs. with stirring under atmospheric pressure.

The reaction mixture was cooled to 0° C. in the ice bath, and kept at the same temperature for 2 hrs. with stiring.

The crystalline product was precipitated and separated by filtration of the reaction mixture.

The results were shown in the following table.

In the experiments of No. 3, 4, and 5, the crude lysine methyl ester dihyhdrochloride was purified to a purity of 98% by washing with chilled methanol.

Table 1

| Exp. No. | Water/Methanol Molar ratio | Yield[a] (mole %) | Raw Yield[b] (wt %) | Purity[c] (mole %) |
|---|---|---|---|---|
| 5 - 1 | 0.0 (120° C.) | 23 | 20 | 23 |
| 5 - 2 | 0.01 | 30 | 28 | 30 |
| 5 - 3 | 0.25 | 60 | 35 | 84 |
| 5 - 4 | 0.50 | 64 | 35 | 94 |
| 5 - 5 | 2.00 | 50 | 10 | 90 |
| 5 - 6 | 4.00 | 30 | 0 | — |

[a]Yield means the molar ratio of lysine methyl ester dihydrochloride in the reaction mixture to initial α-amino-ξ-caprolactam hydrochloride.
[b]Raw Yield means ratio of the weight of crystalline raw product separated from the reaction mixture to 23.31 grs.
[c]Purity means the content of lysine methyl ester dihydrochloride in the isolated crystalline material measured by NMR spectrum in $D_2O$ solvent.

EXAMPLE 6

The same reaction as Example 5 No. 5 was repeated, using 230 grs. of ethanol (5 moles) instead of methanol.

The reaction mixture, thus obtained, was cooled with stirring in the ice bath to crystallize out the crystalline product. 15.93 grs. of crystalline product was obtained by filtration. (Raw yield 62%)

EXAMPLE 7

25.2 grs. of water (1.4 moles) was added to the solution containing 12.82 grs. of α-amino-ε-caprolactam (0.1 mole), 500 grs. of cyclohexanol (5 moles), and 76.09 grs. of p-toluensulfonic acid monohydrate (0.4 mole).

The solution, thus prepared, was charged into the 1 liter four necked flask equipped with cooler, and stirred at 150° C. for 20 hrs. under atmospheric pressure.

After the reaction is over, cyclohexanol and water were evaporated from the reaction mixture under the reduced pressure; the remaining solid was dissolved in 50 ml of methanol.

The methanol solution was passed through the anion exchange column, i.e. IRA-900 Amberlite anion exchange resin, OH type, feed from water before use, and then lysine cyclohexyl ester was eluted by addition of 100 ml of methanol.

The eluted product was neutralized by HCl gas in the dry-ice-methanol bath. After the evaporation of solvent and following drying in the vacuum oven, 10.58 grs. of lysine cyclohexyl ester monohydrochloride was obtained. (Raw yield 40%) m.p. 169°–179° C.

EXAMPLE 8

3.6 grs. of water (0.2 mole) was added to the solution containing 12.82 grs. of α-amino-ε-caprolactam (0.1 mole), 651 grs. of n-octyl alcohol, and 76.09 grs. of p-toluensulfonic acid monohydrate (0.4 mole).

The solution, thus prepared, was charged into the same reaction vessel as Example 5, and stirred at 150° C. for 20 hrs. under atmospheric pressure.

After the reaction, about 500 grs. of n-octyl alcohol was evaporated from the reaction mixture under reduced pressure, and lysine n-octyl ester di-p-toluensulfonate was crystallized by the addition of about 100 grs. of acetone. 20.26 grs. of crystalline materials was obtained. (Raw yield 30%)

EXAMPLE 9

41.16 grs. of α-amino-ε-caprolactam hydrochloride (0.25 mole) was added into the solution containing 128 grs. of methanol (4 moles), 18 grs. of water (2 moles), 41.46 grs. of hydrogenchloride (1.136 moles).

The solution was charged into the same reaction vessle as used in Example 5, and stirred for 5 hrs. at the reflux temperature.

After the reaction, the reaction mixture was cooled to 0° C., and kept at the same temperature for 2 hrs. with stirring. 18 grs. of crystal was separated from the cooled reaction mixture by filtration. (Raw yield 31%)

Then, 10.54 grs. of α-amino-ε-caprolactam (0.08 mole), 2.56 grs. of methanol (0.08 mole), and 5.84 grs. of HCl (0.16 mole) were added to the mother liquor, and the thus prepared mixture was stirred for 3 hrs. at the reflux temperature. The reaction mixture was cooled to 0° C., and 17.5 grs. of crystal was obtained by filtration.

What we claim is:
1. A continuous method for producing lysine ester which comprises the steps of
   1. heating α-amino-ε-caprolactam or its salt with an alcohol selected from the group consisting of primary and secondary alcohols having 1 to 10 carbon atoms together with 0.01-2 moles of water per mole of alcohol, in the presence of an acid catalyst at an elevated temperature, said alcohol being present in the amount of 5 to 200 moles per mole of α-amino-ε-caprolactam,
   2. crystallizing out the lysine ester acid salt formed,
   3. recovering said lysine ester salt, and
   4. recycling the resultant part of the reaction mixture to step (1).
2. The method of claim 1 wherein the alcohol is selected from the group consisting of primary and secondary alcohol represented by a general formula R–OH wherein R is alkyl or cycloalkyl radical having 1 to 10 carbon atoms.
3. The method of claim 1 wherein the amount of the alcohol is 5 to 50 moles per mole of α-amino-ε-caprolactam.
4. The method of claim 1 wherein the acid catalyst is hydrochloric acid.
5. The method of claim 1 wherein the α-amino-ε-caprolactam is fed to the reactor in a form of a salt with the acid used as the catalyst.
6. The method of claim 1 wherein the amount of water is 0.03 to 1.5 moles per mole of the alcohol.
7. The method of claim 4 wherein the amount of hydrochloric acid is 0.05 to 1.00 per mole of the alcohol.
8. The method of claim 1 wherein the alcohol is methanol or ethanol.
9. The method of claim 1, wherein said alcohol has 1-3 carbon atoms.

* * * * *

UNITED STATES PATENT AND TRADEMARK OFFICE
CERTIFICATE OF CORRECTION

PATENT NO. : 4,154,956
DATED : May 15, 1979
INVENTOR(S) : Toshiaki Ueda et al

It is certified that error appears in the above-identified patent and that said Letters Patent are hereby corrected as shown below:

Col. 3, line 57, after the word "material" insert --was dissolved--.

Col. 5, line 3 below Table 1, after "raw" insert --material--.

Col. 6, line 14, delete "crystal" and insert --crystalline material--.

Col. 6, line 21, delete "crystal" and insert --crystalline material--.

Signed and Sealed this

Second Day of October 1979

[SEAL]

Attest:

RUTH C. MASON
Attesting Officer

LUTRELLE F. PARKER
Acting Commissioner of Patents and Trademarks